US006696083B1

(12) United States Patent
Paradissis et al.

(10) Patent No.: US 6,696,083 B1
(45) Date of Patent: Feb. 24, 2004

(54) VITAMIN/NUTRIENT DOSAGE REGIMENTATION

(75) Inventors: George N. Paradissis, St. Louis, MO (US); R. Saul Levinson, Chesterfield, MO (US); Mitchell I. Kirschner, University City, MO (US); Marc S. Hermelin, St. Louis, MO (US)

(73) Assignee: DrugTech Corporation, Wilmington, DE (US)

( * ) Notice: Subject to any disclaimer, the term of this patent is extended or adjusted under 35 U.S.C. 154(b) by 1016 days.

(21) Appl. No.: 09/016,786

(22) Filed: Jan. 30, 1998

Related U.S. Application Data

(63) Continuation of application No. 08/474,070, filed on Jun. 7, 1995, now abandoned, which is a continuation-in-part of application No. 08/262,516, filed on Jun. 20, 1994, now abandoned.

(51) Int. Cl.7 .......................... A61K 9/52; A61K 9/56; A61K 9/22; A61K 9/30
(52) U.S. Cl. ................ 424/451; 424/456; 424/457; 424/463; 424/464; 424/468; 424/474; 424/630; 424/641; 424/646; 424/702; 514/52; 514/251; 514/356; 514/474; 514/725

(58) Field of Search ................... 424/440, 451, 424/456, 457, 463, 464, 468, 474, 630, 641, 646, 702, 52; 514/356, 251, 474, 725

(56) References Cited

U.S. PATENT DOCUMENTS

| | | | | | |
|---|---|---|---|---|---|
| 4,042,698 | A | * | 8/1977 | Zappia | 431/475 |
| 4,752,479 | A | * | 6/1988 | Briggs | 424/472 |
| 4,806,359 | A | * | 2/1989 | Radebaugh | 424/470 |
| 5,118,505 | A | * | 6/1992 | Koltringer | 424/195.1 |
| 5,204,116 | A | * | 4/1993 | Edgren | 428/473 |
| 5,254,572 | A | * | 10/1993 | Serfontein | 514/345 |
| 5,308,627 | A | * | 5/1994 | Umbdenstock | 424/639 |

* cited by examiner

Primary Examiner—Gollamudi S. Kishore
(74) Attorney, Agent, or Firm—Blackwell Sanders Peper Martin, LLP

(57) ABSTRACT

The efficacy of vitamins and other nutritional agents in treating and preventing various disease states is improved by administering therapeutically effective levels of these agents on a substantially continuous, 24-hour basis. The concentration of lipid peroxides formed by the autoxidation of lipids, and the concentration of oxygen free radicals, are reduced by continuously administering antioxidant agents. The regeneration of nerve tissue is improved by continuously administering at least one pharmaceutically-acceptable B complex vitamin.

12 Claims, No Drawings

VITAMIN/NUTRIENT DOSAGE REGIMENTATION

RELATED APPLICATION

This application is a continuation application of U.S. patent application Ser. No. 08/474,070 filed Jun. 7, 1995 now abandoned, which is a continuation-in-part application of U.S. patent application Ser. No. 08/262,516, filed Jun. 20, 1994, abandoned, the entire contents of both applications which are hereby incorporated in their entirety.

BACKGROUND OF THE INVENTION

1. Field of the Invention

The present invention relates to methods for treating disease states, and particularly to a method for the prevention and treatment of certain disease states in humans by the continuous administration of vitamins and minerals.

2. Description of Related Art

Vitamin and mineral preparations are commonly administered to treat specific medical conditions or as general nutritional supplements. Recent studies have elucidated the important physiological roles played by vitamins and minerals, and established a correlation between deficiencies of these nutrients and the etiologies of certain disease states in humans.

In this regard, Diplock, "Antioxidant Nutrients and Disease Prevention: An Overview," *Am. J. Clin. Nutr.*, 53:189–193 (1991) describes the possible use of antioxidant nutrients to treat disease states which may be associated with free radical events in human physiology.

An article by Becker et al. in *Neurochirurgia*, Vol. 33 (1990), pages 113–121 discloses a study of the degenerative and regenerative changes in the saphenous nerve of rabbits following systematic treatment with a combination of the Vitamins $B_1$, $B_6$, and $B_{12}$, in comparison with a control group. The data presented show that the degeneration of axons are lower in the group treated with these vitamins.

Varma, "Scientific Basis for Medical Therapy of Cataracts by Antioxidants," *Am. J. Clin. Nutr.*, Vol. 53 (1991), pages 335S–345S, suggests that exposure of animals and humans to oxyradicals may constitute a significant risk factor. The article teaches that nutritional and metabolic antioxidants such as ascorbate, vitamin E, and pyruvate may be useful for prophylaxis or therapy against cataracts.

DiMascio et al., "Antioxidant Defense Systems: the Role of Carotenoids, tocopherols, and Thiols," *Am. J. Clin. Nutr.*, Vol. 53 (1991), pages 194S–200S, suggests that aerobic metabolism involves the generation of oxygen species capable of damaging DNA, proteins, carbohydrates, and lipids. These reactive oxygen species are said to include the superoxide anion radical, hydrogen peroxide, the hydroxyl radical, and singlet molecular oxygen. The paper teaches that tocopherols function as efficient scavengers of hydroperoxyl radicals in biological membranes. The antioxidant functions of glutathione, the carotenoids, and the thiols, are also discussed.

Burton et al., "Vitamin E: Antioxidant Activity, Biokinetics, and Bioavailability," *Annu. Rev. Nutr.*, Vol. 10 (1990), pages 357–382, describes methods for studying the biokinetics and bioavailability of vitamin E.

While the foregoing references, which are incorporated herein by reference, illustrate the potential benefits that may be attained by the administration of vitamins and other nutrients, it would still be desirable to provide a means for improving the efficacy of known vitamin dosage forms and treatment regimens. For example, because vitamins are rapidly absorbed by the body, administration of conventional vitamin dosage forms results in low bioavailability and corresponding poor treatment efficacies. Effective treatment with water soluble vitamins, particularly vitamin C and the B vitamins, poses a particular problem because these vitamins are not stored in the body.

SUMMARY OF THE INVENTION

The invention is based on the discovery that the efficacy of vitamins and other nutritional agents in treating and preventing various disease states may be improved by administering therapeutically effective levels of these agents on a substantially continuous, i.e., over 24-hour period.

Thus, the invention contemplates a method of reducing the concentration of lipid peroxides formed by the autoxidation of lipids in a human, which comprises administering to the human, on a substantially continuous 24-hour basis, a therapeutically effective amount of a pharmaceutically-acceptable antioxidant agent.

Similarly, a second aspect of the invention relates to a method of reducing the concentration of oxygen free radicals in a human, which comprises administering to the human, on a substantially continuous 24-hour basis, a therapeutically effective amount of a pharmaceutically-acceptable antioxidant agent. Examples of oxygen free radicals include: superoxide anion radicals, hydroxyl radicals, peroxo radicals, and singlet molecular oxygen.

Antioxidant agents which may be employed in accordance with the above-described methods include antioxidant minerals, carotenoids, Vitamin E, Vitamin A, Vitamin C, thiols, and mixtures thereof. Vitamins E and C are preferred.

According to a third aspect of the invention, a method of improving the regeneration of nerve tissue in a human is provided, which comprises administering to the human, on a substantially continuous 24-hour basis, a therapeutically effective amount of at least one pharmaceutically-acceptable B complex Vitamin.

The substantially continuous 24-hour administration of the pharmaceutical agent may be achieved by administering the agent in multiple dosages during the daytime and at night. Continuous intravenous or similar method of administration is also possible. Preferably, however, substantially continuous 24-hour administration of the pharmaceutical agents is achieved by administering to the human a controlled release dosage form containing the pharmaceutical agent. In this regard, the controlled release dosage form may be administered about once every 24 hours so as to provide controlled release of the pharmaceutical agent over 24-hour period. Alternatively, the controlled release dosage form may be administered about twice every 24 hours so as to provide controlled release of the pharmaceutical agent over a 24-hour period. Dosage forms providing other than 12- or 24-hour controlled release of the nutritional agent may be employed, provided that therapeutically effective levels of the agents are maintained over a 24 hour period.

Thus, the invention permits the efficacious treatment and prevention of various disease states by maintaining therapeutically effective blood levels of vitamins and other nutritional agents over a substantially continuous, 24-hour dosing period. The inventive method overcomes the problems of rapid absorption and low bioavailability characteristic of conventional vitamin therapies.

DESCRIPTION OF THE PREFERRED EMBODIMENTS

Water soluble vitamins in conventional dosage forms and regimentation are absorbed by the upper small intestine and depleted from the system within about 3 to 4 hours after administration. Current vitamin dosage regimentation typically involves the administration of vitamins once in the morning.

The efficiency of vitamins and other nutritional agents in treating and preventing various disease states has been found to be improved by administering therapeutically effective levels of these agents on a substantially continuous, 24-hour basis.

According to a first aspect of the invention, a method of reducing the concentration of lipid peroxides formed by the autoxidation of lipids in a human is provided, which comprises administering to the human, on a substantially continuous 24-hour basis, a therapeutically effective amount of a pharmaceutically-acceptable antioxidant agent.

This therapy is believed to be useful in preventing the oxidative and enzymatic degradation of cholesterol in the body which results in the formation of very low density lipids (VLDL). These VLDL compounds are not desirable in that they tend to plaque within the vascular system, eventually leading to arteriosclerotic disease. The continuous administration of antioxidant agents prevents the formation of VLDL, thereby preventing the formation of arteriosclerotic plaque.

Useful antioxidant agents for purposes of the invention may be selected from the group consisting of antioxidant minerals, carotenoids, Vitamin E, Vitamin A, Vitamin C, thiols, and mixtures thereof. Vitamins E and C are preferred.

Antioxidant minerals include those selected from the group consisting of manganese, magnesium, copper, zinc, selenium, and mixtures thereof, with selenium being preferred.

Useful pharmaceutically acceptable magnesium compounds include any of the well-known magnesium supplements, such as magnesium hydroxide, magnesium sulfate, magnesium oxide, magnesium stearate, and magnesium carbonate.

Useful pharmaceutically acceptable calcium compounds include any of the well-known calcium supplements, such as Calcium Carbonate, Calcium Phosphate, Calcium Citrate, Calcium Sulfate, Calcium Oxide, Calcium Hydroxide, Calcium Apatite, Calcium Citrate-Maleate, Calcium Lactate, Calcium Levulinate and the like.

Useful pharmaceutical acceptable zinc compounds include zinc sulfate, zinc chloride, and zinc oxide, with zinc sulfate being preferred.

Pharmaceutically acceptable copper compounds include cupric oxide, cupric sulfate, and cupric gluconate.

Carotenoids which may be employed according to the invention may be selected from the group consisting of lycopene, Beta-carotene, and mixtures thereof.

A preferred thiol for use according to the invention is glutathione.

The substantially continuous 24-hour administration of the pharmaceutical agent may be achieved by administering the agent in multiple dosages during the daytime and at night. Continuous intravenous or similar method of administration is also possible. Preferably, however, substantially continuous 24-hour administration of the pharmaceutical agents is achieved by administering to the human a controlled release dosage form containing the pharmaceutical agent. In this regard, the controlled release dosage from may be administered about once every 24 hours so as to provide controlled release of the pharmaceutical agent over a 24-hour period. Alternatively, the controlled release dosage form may be administered about twice every 24 hours so as to provide controlled release of the pharmaceutical agent over a 24-hour period.

Suitable controlled release forms may be prepared using materials and techniques that are well-known in the art. Generally, controlled release delivery systems include a coating or matrix of a polymeric material such as cellulose ethers selected from hydroxypropyl methylcellulose, methylcellulose, ethylcellulose carboxymethlcellulose, and the like; cellulose esters such as cellulose acetate, cellulose acetate phthalate, and cellulose nitrate; acrylate and methacrylate copolymers; and similar materials, in an amount sufficient to provide controlled release of the active agent over the desired time period. Preferred controlled release dosage forms are 12- and 24-hour controlled release drug delivery systems, which have been found to provide the greatest patient compliance with the 24-hour treatment regimen according to the invention.

Examples of suitable controlled release drug delivery forms are described in U.S. Pat. Nos. 5,137,733; 5,126,145; 5,122,367; 5,102,666; 5,091,189; 5,084,287; 5,081,111; 5,079,009, 5,079,007; 5,073,543; 5,068,220; 5,068,112; 5,055,303; 5,051,263; 5,049,395; 5,041,292; 5,035,894; 5,008,114; 5,004,614; 4,976,949; 4,970,075; 4,952,402; 4,913,906; 4,892,742; 4,891,223; 4,861,598; 4,847,077; 4,756,911; 4,666,705; 4,610,870; and 4,505,890. The disclosures of these patents are incorporated herein by reference. The above patents illustrate controlled release drug delivery systems which may be useful in carrying out the invention; however, the invention is not intended to be limited by the specific drug delivery systems disclosed therein.

A second aspect of the invention contemplates a method of reducing the concentration of oxygen free radicals in a human, which comprises administering to the human, on a substantially continuous 24-hour basis, a therapeutically effective amount of a pharmaceutically-acceptable antioxidant agent.

Oxidative reactions caused by circulating oxygen free radicals have been implicated as the cause of irreversible chemical changes that result in compromise of structural elements of the body, particularly DNA, proteins, carbohydrates, and lipids. These changes can be characterized as the "aging" process. Additionally, some disease states wherein organ dysfunction occurs seem to be related to the presence of oxygen free radicals. These potentially destructive reactive oxygen species include the superoxide anion radical, hydrogen peroxide, the hydroxyl radical, and singlet molecular oxygen.

The continuous administration of antioxidant vitamins is contemplated by the invention as a means for preventing the potential destruction which is now understood to be caused by oxygen free radicals in the human body.

The antioxidant vitamins, particularly Vitamin C and the B Vitamins, are believed to prevent or mediate the formation of cataracts caused by oxygen free radicals. Maintaining continuous adequate levels of these vitamins according to the invention is believed to improve the body's resistance to and recovery from cataracts.

Therapeutically useful antioxidant agents again include those selected from the group consisting of antioxidant minerals, carotenoids, Vitamin E, Vitamin A, Vitamin C, thiols, and mixtures thereof. Vitamins C and E are the preferred antioxidant agents utilized according to the invention. Controlled release dosage forms described above, especially 12- and 24-hour controlled release dosage forms, are also preferred to carry out this aspect of the invention.

According to a third aspect of the invention, a method of improving the regeneration of nerve tissue in a human is provided, which comprises administering to the human, on a substantially continuous 24-hour basis, a therapeutically effective amount of at least one pharmaceutically-acceptable B complex vitamin.

The B complex Vitamins have been identified as major elements involved in the repair and maintenance of the nervous system. It has been noted that significant nerve tissue repair occurs during sleep, and in fact sleep physiologists have speculated that the major function of sleep is to allow the regeneration, maintenance, and, repair of nerve tissue. The inventive process of continuous, 24-hour administration of vitamins therefore optimizes the natural nerve repair process which occurs during sleep. Conventional administration of vitamins during the daytime fails to account for the significant need for B complex Vitamins at night.

B complex Vitamins which are useful for purposes of the invention include those selected from the group consisting of Vitamin $B_1$, Vitamin $B_6$, Vitamin $B_{12}$, and mixtures thereof.

The nutritional supplements of the invention may be provided in any suitable dosage form known in the art. For example, the compositions may be incorporated into tablets, powders, granules, beads, chewable lozenges, capsules, liquids, or similar conventional dosage forms, using conventional equipment and techniques known in the art. As discussed above, 12- and 24-hour controlled release drug delivery systems are the preferred means for achieving a substantially continuous administration of nutritional agents over a 24-hour period.

It is also possible in the present formulations to combine various forms of extended release particles or coatings along with immediate release particles or coatings to deliver the various vitamins and mineral supplements over various times during the twenty-four hours of release. For example, certain agents such as Thiamine, Niacinamide, Pyridoxine, Ascorbic Acid, Folic Acid, Iron and Riboflavin could be released over an extended period of time from six hours up to twenty-four hours while other agents such as Beta-carotene, Vitamin A, Vitamin $D_3$, Vitamin $B_{12}$, Biotin, Pantothenic Acid, Copper, Zinc, Magnesium, Potassium, Iodine, Chromium, Molybdenum and Selenium can be administered as immediate release. The ability to obtain extended and immediate release characteristics is performed using well known procedures and techniques available to the ordinary skilled artisan.

For preparing compositions from the compounds described by this invention, inert, pharmaceutically acceptable carriers can be used which are either solid or liquid. Solid form preparations include powders, tablets, dispersible granules, capsules, and cachets.

Furthermore, the dosage form can be in the form of a bi-layer tablet composed of at least one extended-release layer and at least one immediate-release layer. Additionally, the bi-layer tablet can be coated for ease of administration or can be enteric coated to reduce any gastric irritation and the unpleasant "burping" produced by the vitamins and minerals. Also, multi-particulate design of extended-release and immediate-release components can be enteric coated and compressed into a tablet or filled into hard or soft gelatin capsules.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compounds. In the tablet the active compound is mixed with carrier having the necessary binding properties in suitable proportions and compacted in the shape and size desired. The powders and tablets preferably contain from 5 or 10 to about 90 percent of the active ingredient. Suitable solid carriers are magnesium carbonate, magnesium stearate, talc, sugar, lactose, pectin, dextrin, starch, microcrystalline cellulose, gelatin, tragacanth, methylcellulose, sodium carboxymethylcellulose, a low melting wax, coca butter, and the like. The term "preparation" is intended to include the formulation of the active compounds with encapsulating material as carrier providing a capsule in which the active component (with or without other carriers) is surrounded by carrier, which is thus in association with it. Similarly, cachets are included. Tablets, powders, cachets, and capsules can be used a solid dosage forms suitable for oral administration.

Liquid form preparations include solutions, suspensions, and emulsions. As an example, water or water/propylene glycol solutions for parenteral injection may be used. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses are may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the preparations are in unit dosage form. In such form, the preparation is subdivided into unit doses containing appropriate quantities of the active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied according to the particular application and the potency of the active ingredients.

Determination of the proper dosage for a particular situation is within the skill of the art. For convenience, the total daily dosage may be divided and administered in portions during the day if desired or at one time, morning, afternoon, night as well as biphasic, triphasic, etc. Controlled and uncontrolled release formulations are also contemplated.

When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbents, such as silicon dioxide; preservatives, such as methylparaben, propylparaben, and sodium benzoate; surfactants, such as solium lauryl sulfate, polysorbate 80, and the like; and colorants, such as F.D. & C dyes and lakes.

EXAMPLE 1

This example demonstrates the preparation of a pharmaceutically acceptable antioxidant agent for reducing the concentration of lipid peroxides in a human. The preparation was prepared with the components set forth in Table I.

TABLE I

| Component | Trimester I | Trimester II | Trimester III |
|---|---|---|---|
| Calcium, mg. | 160–240 | 240–360 | 320–480 |
| Vitamin D, I.U. | 320–480 | 360–540 | 400–600 |
| Beta-carotene, I.U. | 200–600 | 300–900 | 400–1200 |
| Vitamin $B_{12}$, mcg | 9.6–14.4 | 9.6–14.4 | 9.6–14.4 |
| Vitamin $B_6$, mg. | 16–24 | 8–12 | 8–12 |
| Vitamin $B_3$, mg. | 16–24 | 16–24 | 16–24 |
| Vitamin $B_2$, mg | 2.7–4.0 | 2.7–4.0 | 2.7–4.0 |
| Vitamin $B_1$, mg | 2.4–3.6 | 2.4–3.6 | 2.4–3.6 |
| Vitamin E, I.U. | 20–30 | 24–36 | 24–36 |
| Iron, mg | 14–22 | 48–72 | 72–108 |
| Zinc, mg | 16–24 | 16–24 | 16–24 |
| Vitamin C, mg | 95–145 | 95–145 | 95–145 |
| Molybdenum, mcg | 20–30 | 20–30 | 20–30 |
| Chromium, mcg | 40–60 | 40–60 | 40–60 |
| Vitamin A I.U. | 1,800–5,400 | 2,700–8,000 | 3,600–10,000 |
| Potassium, mg | 40–60 | 40–60 | 40–60 |
| Pantothenic Acid, mg | 12–18 | 12–18 | 12–18 |
| Folic Acid, mg | 0.8–1.2 | 0.8–1.2 | 0.8–1.2 |
| Biotin, mcg | 40–60 | 40–60 | 40–60 |
| Copper, mg | 1.6–2.4 | 1.6–2.4 | 1.6–2.4 |
| Iodine, mcg | 120–180 | 120–180 | 120–180 |
| Magnesium, mg | 20–30 | 40–60 | 80–120 |
| Selenium, mcg | 50–70 | 50–70 | 50–70 |
| Phosphorous, mg | 320–480 | 320–480 | 320–480 |
| Sodium Starch Glycolate, mg | 140–240 | 140–240 | 140–240 |
| Ethyl Cellulose, mg | 400–620 | 400–620 | 400–620 |
| Stearic Acid, mg | 170–300 | 170–300 | 170–300 |
| Microcrystalline Cellulose, mg | 200–380 | 200–380 | 200–380 |
| Silicon Dioxide, mg | 10–40 | 10–40 | 10–40 |
| Magnesium Stearate, mg | 10–24 | 10–24 | 10–24 |

EXAMPLE 2

This example demonstrates the preparation of a pharmaceutically acceptable antioxidant agent for reducing the concentration of lipid peroxides in a human. The preparation was prepared with the components set forth in Table II.

TABLE II

| Component | Lactating | Nonlactating | Menopause |
|---|---|---|---|
| Calcium, mg | 320–480 | 160–240 | 320–480 |
| Vitamin D, I.U. | 400–600 | 320–480 | 320–480 |
| Beta-carotene, I.U. | 400–1200 | 250–750 | 250–750 |
| Vitamin $B_{12}$, mcg | 9.6–14.4 | 9.6–14.4 | 20–30 |
| Vitamin $B_6$, mg | 8–12 | 8–12 | 2.4–3.6 |
| Vitamin $B_3$, mg | 20–30 | 20–30 | 16–24 |
| Vitamin $B_2$, mg | 2.7–4.0 | 2.7–4.0 | 1.3–2.0 |
| Vitamin $B_1$, mg | 3.2–4.8 | 3.2–4.8 | 1.2–1.8 |
| Vitamin E, I.U. | 24–36 | 24–36 | 70–110 |
| Iron, mg | 24–43 | 39–42 | 7–11 |
| Zinc, mg | 20–30 | 20–30 | 16–24 |
| Vitamin C, mg | 95–145 | 95–175 | 190–300 |
| Molybdenum, mcg | 20–30 | 40–60 | 40–60 |
| Chromium, mcg | 40–60 | 80–120 | 80–120 |
| Vitamin A, I.U. | 3,600–10,000 | 3,600–5,400 | 3,600–5,400 |
| Potassium, mg | 40–60 | 40–60 | 64–96 |
| Pantothenic Acid, mg | 12–18 | 8–12 | 8–12 |
| Folic Acid, mg | 0.8–1.2 | 0.4–0.8 | 0.4–0.6 |
| Biotin, mcg | 40–60 | 240–360 | 240–360 |
| Copper, mg | 1.6–2.4 | 1.6–2.4 | 1.6–2.4 |
| Iodine, mcg | 120–180 | 120–180 | 120–180 |
| Magnesium, mg | 160–240 | 160–240 | 160–240 |
| Selenium, mcg | 50–70 | 50–70 | 50–70 |
| Phosphorous, mg | 320–480 | 160–240 | 320–480 |
| Sodium Starch Glycolate, mg | 140–240 | 140–240 | 140–240 |
| Ethyl Cellulose, mg | 400–620 | 400–620 | 400–620 |
| Stearic Acid, mg | 170–300 | 300–490 | 300–490 |
| Microcrystalline Cellulose, mg | 200–380 | 280–440 | 280–440 |
| Silicon Dioxide, mg | 10–40 | 20–50 | 20–50 |
| Magnesium Stearate, mg | 10–24 | 14–28 | 14–28 |

The invention being thus described, it will be apparent that the same may be varied in many ways. Such variations are not to be regarded as a departure from the spirit and scope of the invention, and all such modifications are intended to be within the scope of the appended claims.

We claim:

1. A method of optimizing the regeneration, maintenance or repair of nerve tissue that occurs naturally during sleep in a human, which comprises: administering to the human a therapeutically effective amount of a composition consisting essentially of at least one water-soluble B complex Vitamin independently selected from the group consisting of Vitamin $B_1$, (Thiamine), Niacinamide, Folic Acid, Riboflavin (Vitamin $B_2$), Pantothenic Acid (Vitamin $B_5$), Vitamin $B_6$, Pyridoxine, Vitamin $B_{12}$, wherein the water-soluble B complex Vitamin is administered at night to optimize the regeneration, maintenance or repair of nerve tissue that occurs naturally during sleep resulting from the presence of said B complex Vitamin.

2. The method of claim 1, wherein at least one B complex vitamin is selected from the group consisting of Vitamin $B_1$, Vitamin $B_6$, Vitamin $B_{12}$, and mixtures thereof.

3. The method of claim 1, wherein a substantially continuous 24-hour administration of the B complex vitamin is achieved by administering to the human a controlled release dosage form containing the B complex vitamin.

4. The method of claim 3, wherein the controlled release dosage form is administered once every 24 hours so as to provide controlled release of the B complex vitamin over a 24-hour period.

5. The method of claim 1, wherein the therapeutically effective amount of said composition is maintained over a 24 hour period.

6. The method of claim 3, wherein the controlled release dosage form is administered twice every 24 hours so as to provide controlled release of the B complex vitamin.

7. The method of claim 1, wherein the composition is in the form of a bi-layer tablet comprising an extended-release layer and an immediate-release layer.

8. The method of claim 7, wherein the bi-layered tablet is coated for ease of administration or enteric coated to reduce gastric irritation.

9. The method of claim 3, wherein the dosage form is enteric coated and compressed into a tablet or filled into hard or soft gelatin capsules.

10. A method of optimizing the regeneration, maintenance or repair of nerve tissue that occurs naturally during sleep in a human, which comprises: administering to the human, (a) a first composition comprising at least one water-soluble B complex Vitamin independently selected from the group consisting of Thiamine, Niacinamide, Pyridoxine, Folic Acid, and Riboflavin, said first composition being released over an extended period of time from six hours up to twenty-four hours; and (b) a second composition comprising at least one B complex Vitamin selected from the group consisting of Vitamin B12 and Pantothenic Acid, said second composition being administered as an immediate release agent;

wherein the water-soluble B complex Vitamin is administered at night to optimize the regeneration, maintenance or repair of nerve tissue that occurs naturally during sleep resulting from the presence of said B complex Vitamin.

11. The method of claim 10, wherein the first composition also comprises an agent selected from the group consisting of Ascorbic Acid and Iron.

12. The method of claim 10, wherein the second composition also comprises an agent selected from the group consisting of Beta-carotene, Vitamin A, Vitamin $D_3$, Biotin, Copper, Zinc, Magnesium, Potassium, Iodine, Chromium, Molybdenum and Selenium.

* * * * *